United States Patent [19]

Van der Knaap

[11] Patent Number: Plant 6,095

[45] Date of Patent: Feb. 2, 1988

[54] CHRYSANTHEMUM PLANT NAMED IMPALA

[75] Inventor: Jacques C. M. Van der Knaap, De Lier, Netherlands

[73] Assignee: Fides, Handelskwekerij, De Lier, Netherlands

[21] Appl. No.: 821,535

[22] Filed: Jan. 22, 1986

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Schwartz, Jeffery, Schwaab, Mack, Blumenthal & Evans

[57] ABSTRACT

A Chrysanthemum plant named Impala particularly characterized by its flat capitulum form; single daisy capitulum type; pink ray floret color; diameter across the face of the capitulum of 45–75 mm. and yellow-green to yellow disc florets.

1 Drawing Figure

The present invention comprises a new and distinct cultivar of Chrysanthemum, botanically known as *Dendranthema morifolium*, Ramat., previously *Chrysanthemum morifolium*, Ramat., and referred to by the cultivar name Impala.

Impala is a product of a planned breeding program which had the objective of creating new Chrysanthemum cultivars with single daisy capitulum type, pink ray floret color, 9 week response and the ability to produce commercially acceptable quality in year around cut mum programs. Such traits in combination were not present or needed improvement in previously available commercial cultivars.

Impala was originated from a hybridization made in a controlled breeding program in De Lier, The Netherlands in 1981. The female parent was Parliament, an unpatented cultivar. The male parent of Impala was Horim, also unpatented. Impala was discovered and selected as one flowering plant within the progeny of the stated cross by Jacques C. M. Van der Knaap in June of 1982, in a controlled environment in De Lier, The Netherlands.

The first act of asexual reproduction of Impala was accomplished when vegetative cuttings were taken from the initial selection in July of 1982 in a controlled environment in De Lier, The Netherlands by a technician working under formulations established and supervised by Jacques C. M. Van der Knaap. Horticultural examination of selected units initiated in November of 1982 has demonstrated that the combination of characteristics as herein disclosed for Impala are firmly fixed and are retained through successive generations of asexual reproduction.

Impala has not been observed under all possible environmental conditions. The phenotype may vary significantly with variations in environment such as temperature, light intensity and day length. The following observations, measurements and comparisons describe plants grown in De Lier, The Netherlands under greenhouse conditions which approximate those generally used in commercial greenhouse practice.

The following traits have been repeatedly observed and are determined to be basic characteristics of Impala which, in combination, distinguish this Chrysanthemum as a new and distinct cultivar:

1. Flat capitulum form.
2. Single, daisy capitulum type.

3. Pink ray floret color.
4. Diameter across the face of the capitulum is 45–75 mm.
5. Yellow-green (immature) to yellow (mature) disc florets.

Of the many commercial cultivars known to the present inventor, the most similar in comparison to Impala is Horim, the male parent. In comparison to Horim, Impala has more vigor, the ray florets are more pink in color, and it has a shorter response. The flower type and capitulum form of Impala are similar to those same characteristics of Horim.

The accompanying photographic drawing shows typical inflorescence and foliage characteristics of Impala. The photograph is in black and white, with two flowers being colored to accurately depict ray and disc floret colors.

In the following description, color references are made to The Royal Horticultural Society Colour Chart. The color values were determined between 11:00 a.m. and 12:00 noon in November of 1982 under natural day light at De Lier, The Netherlands.

Classification:

*Botanical.*—*Dendranhema morifolium*, Ramat., cv Impala.

*Commercial.*—Cut daisy spray.

INFLORESCENCE

A. Capitulum:

*Form.*—Flat.

*Type.*—Daisy.

*Diameter across face.*—45–75 mm.

B. Corolla of ray florets:

*Color (general tonality from a distance of three meters).*—Pink.

*Color (upper surface).*—RHS 56C.

C. Corolla of disc florets:

*Color (mature).*—Yellow.

*Color (immature).*—Yellow-green.

D. Reproductive organs:

*Androecium.*—Present in disc florets, numerous.

*Gynoecium.*—Present in both disc and ray florets; numerous.

PLANT

A. General appearance:

*Height.*—90 cm.

B. Foliage:

*Color* (*upper surface*).—RHS 147A.

*Shape.*—Long lobed and deeply serrated.

I claim:

1. A new and distinct Chrysanthemum plant named

Impala, as described and illustrated, and particularly characterized by its flat capitulum form; single daisy capitulum type; pink ray floret color; diameter across the face of the capitulum of 45–75 mm. and yellow-green to yellow disc florets.

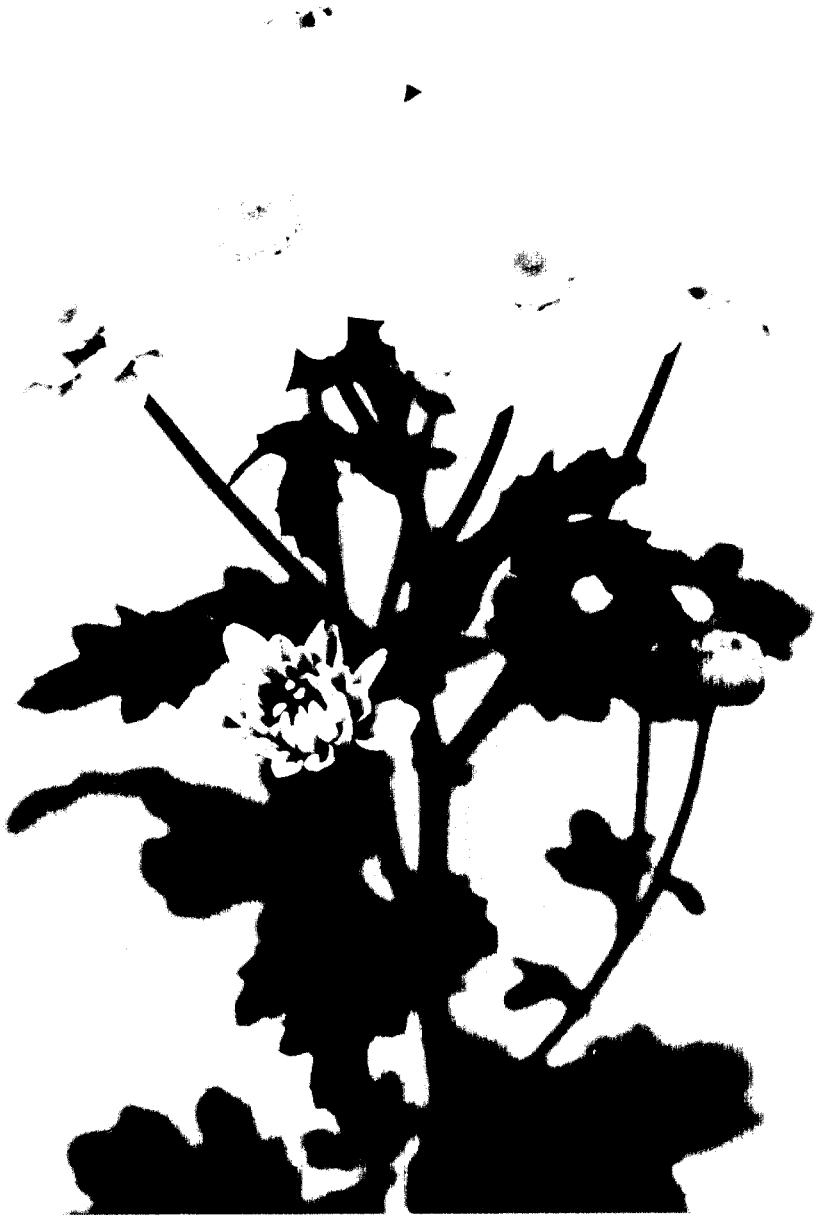

* * * * *